US008030529B2

(12) United States Patent
Wang et al.

(10) Patent No.: US 8,030,529 B2
(45) Date of Patent: Oct. 4, 2011

(54) PROCESS FOR THE PREPARATION OF INTERMEDIATES

(75) Inventors: Linhua Wang, Huddersfield (GB); Kristine Anderson Dolbeare, Semmes, AL (US); Frankie Lee Odom, Bucks, AL (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 163 days.

(21) Appl. No.: 11/815,458

(22) PCT Filed: Feb. 7, 2006

(86) PCT No.: PCT/EP2006/001068
§ 371 (c)(1),
(2), (4) Date: Mar. 10, 2008

(87) PCT Pub. No.: WO2006/084663
PCT Pub. Date: Aug. 17, 2006

(65) Prior Publication Data
US 2009/0023964 A1    Jan. 22, 2009

Related U.S. Application Data

(60) Provisional application No. 60/651,175, filed on Feb. 9, 2005.

(51) Int. Cl.
*C07C 17/00* (2006.01)
(52) U.S. Cl. .................. 570/191; 570/206; 570/207
(58) Field of Classification Search .................. None
See application file for complete search history.

(56) References Cited

U.S. PATENT DOCUMENTS

| 4,822,927 A | 4/1989 | Stepanink et al. |
| 5,681,957 A | 10/1997 | Wolters et al. |

FOREIGN PATENT DOCUMENTS

| DE | 600706 | 7/1934 |
| DE | 1695659 | 12/1971 |
| DE | 4111214 | 10/1992 |
| EP | 0 214 068 B1 | 3/1987 |
| EP | 0214068 | 3/1987 |
| EP | 1375502 | 1/2004 |
| JP | 59112965 | 6/1984 |
| JP | 01-283230 | * 11/1989 |
| JP | 01283230 | 11/1989 |
| WO | 99/47525 A1 | 9/1999 |
| WO | 00/78881 A2 | 12/2000 |
| WO | 0078712 | 12/2000 |
| WO | 02/081472 | 10/2002 |
| WO | 2004/050607 A1 | 6/2004 |

OTHER PUBLICATIONS

Database WPI Section Ch, Week 198951, Derwent Publications Ltd., London, GB; AN 1989-375646, XP0023822741 & JP 01 283230 A (Mitsui Toatsu Chem Inc) Nov. 14, 1989, abstract & Patent Abstracts of Japan, vol. 014, No. 057 (C-0684), Feb. 2, 1990 & JP 01 283230 A (Mitsui Toatsu Chem Inc), Nov. 14, 1989, abstract.
W.A. Cowdrey, et al.: "Sandmeyer and Related Reactions" Quart. Revs. (London), 1952 (6), p. 358-379.
May 2, 2010 EPO Official Office Action for corresponding European application No. 06704443.
Cain J, "Diazo Chemistry—Synthesis and Reactions", 2003, Wexford College Press; extract from Chapter VI: "The reactions of the diazo-compounds (continued)", p. 43.
Hodgson, H.H., "The Sandmeyer Reaction", Chem. Rev., 1947, 40(2), pp. 251-277.
Galli, C., "Radical reactions of arenediazonium ions: an easy entry into the chemistry of the aryl radical", Chem. Rev., 1988, 88(5), pp. 765-792.
Sandmeyer, T., "Ueber die Ersetzung der Amidgruppe durch Chlor in den aromatischen Substanzen", Berichte, 1884, vol. 17, pp. 1633-1635 (in German).
Galli, C., "An investigation of the two-step nature of the Sandmeyer reaction", J. Chem. Soc., Perkin Trans. II, 1981, pp. 1459-1461.
Nonhebel, D.C., and Waters, W.A., "A study of the mechanism of the Sandmeyer reaction", Proceedings of the Royal Society of London, Series A, Mathematical and Physical Sciences, 1957, vol. 242, No. 1228, pp. 16-27.
Francom, P., and Robins, M.J., "Nucleic acid related compounds. 118. Nonaqueous diazotization of aminopurine derivatives. Convenient access to 6-halo and 2,6-dihalopurine nucleosides and 2'-deoxynucleosides with acyl or silyl halides", J. Org. Chem., 2003, 68, pp. 666-669.

(Continued)

*Primary Examiner* — Kamal Saeed
*Assistant Examiner* — Chukwuma O Nwaonicha
(74) *Attorney, Agent, or Firm* — James Cueva

(57) ABSTRACT

The present invention provides a process for the production of intermediate compounds of formula (I), wherein the substituents are as defined herein. The process comprises reacting a substituted aniline with aqueous HX, followed by removal of water by azeotropic distillation and diazotization and pyrolysis with an organic nitrite at elevated temperatures in the absence of a copper catalyst. Alternatively, gaseous HX can be used to substitute aqueous HX in the process. Consequently, a step of water removal by azeotropic distillation can be eliminated. The intermediate compounds of formula I are suitable as intermediates in the preparation of herbicidally active 3-hydroxy-4-aryl-5-oxopyrazoline derivatives.

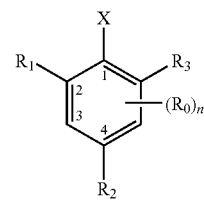

15 Claims, No Drawings

OTHER PUBLICATIONS

Francom, P., et al., "Nucleic acid related compounds. 116. Nonaqueous diazotization of aminopurine nucleosides. Mechanistic considerations and efficient procedures with tert-butyl nitrite or sodium nitrite", J. Org. Chem., 2002, 67, pp. 6788-6796.

Robins, M.J. and Uznanski, B., "Nucleic acid related compounds. 34. Non-aqueous diazotization with tert-butyl nitrite. Introduction of fluorine, chlorine, and bromine at C-2 of purine nucleosides", Can. J. Chem., 1981, 59, pp. 2608-2611.

"Methoden der Organischen Chemie (Houben-Weyl), Band X/3, Stickstoff-Verbindungen I—Teil 3", G. Thieme, Stuttgart, 1965, p. 32, in German.

Ozeki, N., et al., "A new Sandmeyer iodination of 2-aminopurine in non-aqueous conditions: combination of alkali metal iodide and iodine and iodine sources", Heterocycles, 2001, 55(3), pp. 461-464.

Kraska, J., et al., "Studies on the diazotization of aromatic amines with glycol nitrite", Dyes and Pigments, 1990, 12(3), pp. 173-177; Chemical Abstracts abstract thereof (Chem.Abs. Accession No. 1990:141224).

Schmid, H., "The mechanism of diazotization of aromatic amines in nonaqueous solvents", US Dept. Com., Office Tech. Serv., P B Rept., 1960, 154157, 60 pages; Chemical Abstracts abstract thereof (Chem. Abs. Accession No. 1962: 420161).

Schmid, H., and Muhr, G., "Kinetics and mechanism of diazotization. XVII. Kinetics of diazotization in nonaqueous solvents", Monatshefte fuer Chemie., 1960, 91, pp. 1198-1199; Chemical Abstracts abstract thereof in English (Chem. Abs. Accession No. 1961:74155).

"Methoden der Organischen Chemie (Houben-Weyl), Band V/4, Halogenverbindungen", G. Thieme, Stuttgart, 1960, p. 441, in German.

Gabriel, S., Chem. Ber., 1882, vol. 15, pp. 2291+2294+2295 in German).

Gabriel, S., et al., Chem. Ber., 1883, vol. 16, pp. 2036-2039 (in German).

* cited by examiner

PROCESS FOR THE PREPARATION OF INTERMEDIATES

This application is a 371 of International Application No. PCT/EP2006/001068 filed Feb. 7, 2006, which claims priority to U.S. Provisional Application No. 60/651,175 filed Feb. 9, 2005, the contents of which are incorporated herein by reference.

The present invention relates to an improved process for the preparation of substituted benzene derivatives useful as intermediates in the production of herbicidally active substituted 3-hydroxy-4-aryl-5-oxopyrazoline derivatives.

3-Hydroxy-4-aryl-5-oxopyrazolines having herbicidal action and the preparation thereof are described, for example, in WO 92/16510, EP-A-0 508 126, WO 95/01971, WO 96/21652, WO 96/25395, WO 97/02243 and in WO 99/47525, the contents of which are all incorporated by reference.

It has now been discovered that substituted benzene derivatives, key intermediates in the process for preparing herbicidally active substituted 3-hydroxy-4-aryl-5-oxopyrazoline derivatives, can be prepared in high yield with a considerable cost advantage over known processes.

The present invention accordingly relates to preparation of a compound of formula I

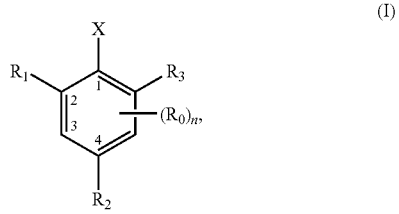

(I)

wherein $R_0$ is, each independently of any other, halogen, $C_1$-$C_6$alkyl, $C_2$-$C_6$alkenyl, $C_2$-$C_6$alkynyl, $C_1$-$C_6$haloalkyl, cyano-$C_1$-$C_6$alkyl, $C_2$-$C_6$haloalkenyl, cyano-$C_2$-$C_6$alkenyl, $C_2$-$C_6$haloalkynyl, cyano-$C_2$-$C_6$alkynyl, hydroxy, hydroxy-$C_1$-$C_6$alkyl, $C_1$-$C_6$alkoxy, nitro, amino, $C_1$-$C_6$alkylamino, di($C_1$-$C_6$alkyl)amino, $C_1$-$C_6$alkylcarbonylamino, $C_1$-$C_6$alkylsulfonylamino, $C_1$-$C_6$alkylaminosulfonyl, $C_1$-$C_6$alkylcarbonyl, $C_1$-$C_6$alkylcarbonyl-$C_1$-$C_6$alkyl, $C_1$-$C_6$alkoxycarbonyl-$C_1$-$C_6$alkyl, $C_1$-$C_6$alkylcarbonyl-$C_2$-$C_6$alkenyl, $C_1$-$C_6$alkoxycarbonyl, $C_1$-$C_6$alkoxycarbonyl-$C_2$-$C_6$alkenyl, $C_1$-$C_6$alkylcarbonyl-$C_2$-$C_6$alkynyl, $C_1$-$C_6$alkoxycarbonyl-$C_2$-$C_6$alkynyl, cyano, carboxyl, phenyl or an aromatic ring that contains 1 or 2 hetero atoms selected from the group consisting of nitrogen, oxygen and sulfur, wherein the latter two aromatic rings may be substituted by $C_1$-$C_3$alkyl, $C_1$-$C_3$haloalkyl, $C_1$-$C_3$alkoxy, $C_1$-$C_3$haloalkoxy, halogen, cyano or by nitro; or $R_0$, together with the adjacent substituents $R_1$, $R_2$ and $R_3$, forms a saturated or unsaturated $C_3$-$C_6$hydrocarbon bridge that may be interrupted by 1 or 2 hetero atoms selected from the group consisting of nitrogen, oxygen and sulfur and/or substituted by $C_1$-$C_4$alkyl;

$R_1$, $R_2$ and $R_3$ are, each independently of the others, hydrogen, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_1$-$C_6$alkoxy-carbonyl-$C_2$-$C_6$alkenyl, $C_1$-$C_6$alkylcarbonyl-$C_2$-$C_6$alkenyl, cyano-$C_2$-$C_6$alkenyl, nitro-$C_2$-$C_6$alkenyl, $C_2$-$C_6$haloalkynyl, $C_1$-$C_6$alkoxycarbonyl-$C_2$-$C_6$alkynyl, $C_1$-$C_6$alkylcarbonyl-$C_2$-$C_6$alkynyl, cyano-$C_2$-$C_6$alkynyl, nitro-$C_2$-$C_6$alkynyl, $C_3$-$C_6$halocycloalkyl, hydroxy-$C_1$-$C_6$alkyl, $C_1$-$C_6$alkoxy-$C_1$-$C_6$alkyl, $C_1$-$C_6$alkylthio-$C_1$-$C_6$alkyl, cyano, $C_1$-$C_4$alkylcarbonyl, $C_1$-$C_6$alkoxycarbonyl, hydroxy, $C_1$-$C_{10}$alkoxy, $C_3$-$C_6$alkenyloxy, $C_3$-$C_6$alkynyloxy, $C_1$-$C_6$haloalkoxy, $C_3$-$C_6$haloalkenyloxy, $C_1$-$C_6$alkoxy-$C_1$-$C_6$alkoxy, mercapto, $C_1$-$C_6$alkylthio, $C_1$-$C_6$haloalkylthio, $C_1$-$C_6$alkylsulfinyl, $C_1$-$C_6$alkylsulfonyl, nitro, amino, $C_1$-$C_6$alkylamino, di($C_1$-$C_6$alkyl)amino or phenoxy in which the phenyl ring may be substituted by $C_1$-$C_3$alkyl, $C_1$-$C_3$haloalkyl, $C_1$-$C_3$alkoxy, $C_1$-$C_3$haloalkoxy, halogen, cyano or by nitro;

$R_2$ also may be phenyl, naphthyl or a 5- or 6-membered aromatic ring that may contain 1 or 2 hetero atoms selected from the group consisting of nitrogen, oxygen and sulfur, wherein the phenyl ring, the naphthyl ring system and the 5- or 6-membered aromatic ring may be substituted by halogen, $C_3$-$C_8$cycloalkyl, hydroxy, mercapto, amino, cyano, nitro or by formyl; and/or the phenyl ring, the naphthyl ring system and the 5- or 6-membered aromatic ring may be substituted by $C_1$-$C_6$alkyl, $C_1$-$C_6$alkoxy, hydroxy-$C_1$-$C_6$alkyl, $C_1$-$C_6$alkoxy-$C_1$-$C_6$alkyl, $C_1$-$C_6$alkoxy-$C_1$-$C_6$alkoxy, $C_1$-$C_6$alkylcarbonyl, $C_1$-$C_6$alkylthio, $C_1$-$C_6$alkylsulfinyl, $C_1$-$C_6$alkylsulfonyl, mono-$C_1$-$C_6$alkylamino, di($C_1$-$C_6$alkyl)amino, $C_1$-$C_6$alkylcarbonylamino, $C_1$-$C_6$alkylcarbonyl-($C_1$-$C_6$alkyl)amino, $C_2$-$C_6$alkenyl, $C_3$-$C_6$alkenyloxy, hydroxy-$C_3$-$C_6$alkenyl, $C_1$-$C_6$alkoxy-$C_2$-$C_6$alkenyl, $C_1$-$C_6$alkoxy-$C_3$-$C_6$alkenyloxy, $C_2$-$C_6$alkenylcarbonyl, $C_2$-$C_6$alkenylthio, $C_2$-$C_6$alkenyl-sulfinyl, $C_2$-$C_6$alkenylsulfonyl, mono- or di-($C_2$-$C_6$alkenyl)amino, $C_1$-$C_6$alkyl($C_3$-$C_6$alkenyl)-amino, $C_2$-$C_6$alkenylcarbonylamino, $C_2$-$C_6$alkenylcarbonyl($C_1$-$C_6$alkyl)amino, $C_2$-$C_6$alkynyl, $C_3$-$C_6$alkynyloxy, hydroxy-$C_3$-$C_6$alkynyl, $C_1$-$C_6$alkoxy-$C_3$-$C_6$alkynyl, $C_1$-$C_6$alkoxy-$C_4$-$C_6$alkynyloxy, $C_2$-$C_6$alkynylcarbonyl, $C_2$-$C_6$alkynylthio, $C_2$-$C_6$alkynylsulfinyl, $C_2$-$C_6$alkynylsulfonyl, mono- or di-($C_3$-$C_6$alkynyl)amino, $C_1$-$C_6$alkyl($C_3$-$C_6$alkynyl)amino, $C_2$-$C_6$alkynylcarbonylamino or by $C_2$-$C_6$alkynylcarbonyl ($C_1$-$C_6$alkyl)amino; and/or the phenyl ring, the naphthyl ring system and the 5- or 6-membered aromatic ring may be substituted by halo-substituted $C_1$-$C_6$alkyl, $C_1$-$C_6$alkoxy, hydroxy-$C_1$-$C_6$alkyl, $C_1$-$C_6$alkoxy-$C_1$-$C_6$alkyl, $C_1$-$C_6$alkoxy-$C_1$-$C_6$alkoxy, $C_1$-$C_6$alkylcarbonyl, $C_1$-$C_6$alkylthio, $C_1$-$C_6$alkylsulfinyl, $C_1$-$C_6$alkylsulfonyl, mono-$C_1$-$C_6$alkylamino, di($C_1$-$C_6$alkyl)amino, $C_1$-$C_6$alkylcarbonylamino, $C_1$-$C_6$alkylcarbonyl($C_1$-$C_6$alkyl)amino, $C_2$-$C_6$alkenyl, $C_3$-$C_6$alkenyloxy, hydroxy-$C_3$-$C_6$alkenyl, $C_1$-$C_6$alkoxy-$C_2$-$C_6$alkenyl, $C_1$-$C_6$alkoxy-$C_3$-$C_6$alkenyloxy, $C_2$-$C_6$alkenylcarbonyl, $C_2$-$C_6$alkenylthio, $C_2$-$C_6$alkenylsulfinyl, $C_2$-$C_6$alkenylsulfonyl, mono- or di-($C_2$-$C_6$alkenyl)amino, $C_1$-$C_6$-alkyl($C_3$-$C_6$alkenyl)amino, $C_2$-$C_6$alkenylcarbonylamino, $C_2$-$C_6$alkenylcarbonyl($C_1$-$C_6$alkyl)amino, $C_2$-$C_6$alkynyl, $C_3$-$C_6$alkynyloxy, hydroxy-$C_3$-$C_6$alkynyl, $C_1$-$C_6$alkoxy-$C_3$-$C_6$alkynyl, $C_1$-$C_6$alkoxy-$C_4$-$C_6$alkynyloxy, $C_2$-$C_6$alkynylcarbonyl, $C_2$-$C_6$alkynylthio, $C_2$-$C_6$alkynylsulfinyl, $C_2$-$C_6$alkynylsulfonyl, mono- or di-($C_3$-$C_6$alkynyl)amino, $C_1$-$C_6$alkyl($C_3$-$C_6$alkynyl)amino, $C_2$-$C_6$alkynylcarbonylamino or $C_2$-$C_6$alkynylcarbonyl($C_1$-$C_6$alkyl)amino; and/or the phenyl ring, the naphthyl ring system and the 5- or 6-membered aromatic ring may be substituted by a radical of formula $COOR_{50}$, $CONR_{51}$, $SO_2NR_{53}R_{54}$ or $SO_2OR_{55}$, wherein $R_{50}$, $R_{51}$, $R_{52}$, $R_{53}$, $R_{54}$ and $R_{55}$ are, each independently of the others, $C_1$-$C_6$alkyl, $C_2$-$C_6$alkenyl or $C_3$-$C_6$alkynyl or halo-, hydroxy-, alkoxy-, mercapto-, amino-, cyano-, nitro-, alkylthio-, alkylsulfinyl- or alkylsulfonyl-substituted $C_1$-$C_6$alkyl, $C_2$-$C_6$alkenyl or $C_3$-$C_6$alkynyl;

X is halogen; and n is 0, 1 or 2.

In the above definitions, halogen is to be understood as fluorine, chlorine, bromine or iodine, preferably fluorine, chlorine or bromine, and most preferably chlorine and bromine. The alkyl groups occurring in the substituent definitions are, for example, methyl, ethyl, n-propyl, isopropyl, n-butyl, sec-butyl, isobutyl or tert-butyl, and the pentyl, hexyl, heptyl, octyl, nonyl, decyl, undecyl and dodecyl isomers.

Haloalkyl groups preferably have a chain length of from 1 to 6 carbon atoms. Haloalkyl is, for example, fluoromethyl, difluoromethyl, difluorochloromethyl, trifluoromethyl, chloromethyl, dichloromethyl, dichlorofluoromethyl, trichloromethyl, 2,2,2-trifluoroethyl, 2-fluoroethyl, 2-chloroethyl, 2,2-difluoroethyl, 2,2-dichloroethyl, 2,2,2-trichloroethyl or pentafluoroethyl, preferably trichloromethyl, difluorochloromethyl, difluoromethyl, trifluoromethyl or dichlorofluoromethyl.

Alkoxy groups preferably have a chain length of from 1 to 6 carbon atoms. Alkoxy is, for example, methoxy, ethoxy, n-propoxy, isopropoxy, n-butoxy, isobutoxy, sec-butoxy, tert-butoxy, or a pentyloxy or hexyloxy isomer, preferably methoxy, ethoxy or n-propoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy or 2,2,2-trichloroethoxy.

There may be mentioned as examples of alkenyl radicals vinyl, allyl, methallyl, 1-methylvinyl, but-2-en-1-yl, pentenyl and 2-hexenyl; preferably alkenyl radicals having a chain length of from 3 to 6 carbon atoms.

There may be mentioned as examples of alkynyl radicals ethynyl, propargyl, 1-methyl-propargyl, 3-butynyl, but-2-yn-1-yl, 2-methylbut-3-yn-2-yl, but-3-yn-2-yl, 1-pentynyl, pent-4-yn-1-yl and 2-hexynyl; preferably alkynyl radicals having a chain length of from 3 to 6 carbon atoms.

Suitable haloalkenyl radicals include alkenyl groups substituted one or more times by halogen, halogen being in particular bromine or iodine and especially fluorine or chlorine, for example 2- and 3-fluoropropenyl, 2- and 3-chloropropenyl, 2- and 3-bromopropenyl, 2,2-difluoro-1-methylvinyl, 2,3,3-trifluoropropenyl, 3,3,3-trifluoropropenyl, 2,3,3-trichloropropenyl, 4,4,4-trifluorobut-2-en-1-yl and 4,4,4-trichlorobut-2-en-1-yl. Preferred alkenyl radicals substituted once, twice or three times by halogen are those having a chain length of from 3 to 6 carbon atoms. The alkenyl groups may be substituted by halogen at saturated or unsaturated carbon atoms.

Alkoxyalkyl groups have preferably from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy or 2,2,2-trichloroethoxy.

Alkenyloxy is, for example, allyloxy, methallyloxy or but-2-en-1-yloxy.

Suitable haloalkenyloxy groups include alkenyloxy groups substituted one or more times by halogen, halogen being in particular bromine or iodine and especially fluorine or chlorine, for example 2- and 3-fluoropropenyloxy, 2- and 3-chloropropenyloxy, 2- and 3-bromopropenyloxy, 2,3,3-trifluoropropenyloxy, 2,3,3-trichloropropenyloxy, 4,4,4-trifluorobut-2-en-1-yloxy and 4,4,4-trichlorobut-2-en-1-yloxy.

Alkynyloxy is, for example, propargyloxy or 1-methylpropargyloxy.

Suitable cycloalkyl substituents contain from 3 to 8 carbon atoms and are, for example, cyclopropyl, cyclobutyl, cyclopentyl, cyclohexyl, cycloheptyl or cyclooctyl. They may be substituted one or more times by halogen, preferably fluorine, chlorine or bromine.

Alkylcarbonyl is especially acetyl or propionyl.

Alkoxycarbonyl is, for example, methoxycarbonyl, ethoxycarbonyl, n-propoxycarbonyl, isopropoxycarbonyl or a butoxycarbonyl, pentyloxycarbonyl or hexyloxycarbonyl isomer, preferably methoxycarbonyl or ethoxycarbonyl.

Alkylthio groups preferably have a chain length of from 1 to 6 carbon atoms. Alkylthio is, for example, methylthio, ethylthio, propylthio, butylthio, pentylthio or hexylthio, or a branched isomer thereof, but is preferably methylthio or ethylthio.

Haloalkylthio is, for example, 2,2,2-trifluoroethylthio or 2,2,2-trichloroethylthio.

Alkylsulfinyl is, for example, methylsulfinyl, ethylsulfinyl, n-propylsulfinyl, isopropylsulfinyl, n-butylsulfinyl, isobutylsulfinyl, sec-butylsulfinyl or tert-butylsulfinyl, preferably methylsulfinyl or ethylsulfinyl.

Alkylsulfonyl is, for example, methylsulfonyl, ethylsulfonyl, n-propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino is, for example, methylamino, ethylamino, n-propylamino, isopropylamino or a butyl-, pentyl- or hexylamine isomer.

Dialkylamino is, for example, dimethylamino, methylethylamino, diethylamino, n-propylmethylamino, dibutylamino or diisopropylamino.

Alkylthioalkyl is, for example, methylthiomethyl, methylthioethyl, ethylthiomethyl, ethylthioethyl, n-propylthiomethyl, n-propylthioethyl, isopropylthiomethyl or isopropylthioethyl.

Phenyl and naphthyl in the definition of $R_2$ and phenoxy in the definition of $R_1$, $R_2$ and $R_3$ may be in substituted form, in which case the substituents may, as desired, be in the ortho-, meta- and/or para-position and, in the case of the naphthyl ring system, in addition in the 5-, 6-, 7- and/or 8-position.

Examples of suitable 5- or 6-membered aromatic rings that contain 1 or 2 hetero atoms selected from the group consisting of nitrogen, oxygen and sulfur in the definition of $R_0$ and $R_2$ are pyrrolidyl, pyridyl, pyrimidyl, triazinyl, thiazolyl, triazolyl, thiadiazolyl, imidazolyl, oxazolyl, isoxazolyl, pyrazinyl, furyl, thienyl, pyrazolyl, benzoxazolyl, benzothiazolyl, quinoxalyl, indolyl and quinolyl. These heteroaromatic radicals may, in addition, be substituted.

Meanings corresponding to those given hereinbefore can also be ascribed to substituents in composite definitions, such as, for example, alkoxy-alkoxy, alkyl-sulfonylamino, alkylaminosulfonyl, phenyl-alkyl, naphthyl-alkyl and heteroaryl-alkyl.

In the definitions for alkylcarbonyl and alkoxycarbonyl, the carbon atom of the carbonyl is not included in the upper and lower limits given for the number of carbons in each particular case.

Preference is given to compounds of formula I wherein n and X are as defined for formula I; $R_0$ is, each independently of any other, halogen, $C_1$-$C_6$alkyl, $C_1$-$C_6$haloalkyl, hydroxy, $C_1$-$C_6$alkoxy, nitro, amino, $C_1$-$C_6$alkylamino, di($C_1$-$C_6$alkyl)amino, $C_1$-$C_6$alkylcarbonylamino, $C_1$-$C_6$alkylsulfonylamino, $C_1$-$C_6$alkylaminosulfonyl, $C_1$-$C_4$alkylcarbonyl, $C_1$-$C_6$alkoxycarbonyl or carboxyl; and $R_1$, $R_2$ and $R_3$ are, each independently of the others, hydrogen, halogen, $C_1$-$C_6$alkyl, $C_2$-$C_6$alkenyl, $C_2$-$C_6$alkynyl, $C_3$-$C_6$cycloalkyl, $C_1$-$C_6$-haloalkyl, $C_2$-$C_6$haloalkenyl, $C_2$-$C_6$haloalkynyl, $C_3$-$C_6$halocycloalkyl, $C_1$-$C_6$alkoxy-$C_1$-$C_6$alkyl, $C_1$-$C_6$alkylthio-$C_1$-$C_6$alkyl, cyano, $C_1$-$C_4$alkylcarbonyl, $C_1$-$C_6$alkoxycarbonyl, hydroxy, $C_1$-$C_{10}$alkoxy, $C_3$-$C_6$alkenyloxy, $C_3$-$C_6$alkynyloxy, $C_1$-$C_6$haloalkoxy, $C_3$-$C_6$haloalkenyloxy, $C_1$-$C_6$alkoxy-$C_1$-$C_6$alkoxy, mercapto, $C_1$-$C_6$alkylthio, $C_1$-$C_6$haloalkylthio, $C_1$-$C_6$alkylsulfinyl, $C_1$-$C_6$alkylsulfonyl, nitro, amino, $C_1$-$C_4$alkylamino or di($C_1$-$C_4$alkyl)amino.

Preference is given also to compounds of formula I wherein $R_1$, $R_2$ and $R_3$ are, each independently of the others, hydrogen, halogen, $C_1$-$C_6$alkyl, $C_1$-$C_4$haloalkyl, $C_2$-$C_4$alkenyl, $C_2$-$C_4$haloalkenyl, $C_2$-$C_4$alkynyl, $C_3$-$C_6$cycloalkyl, $C_1$-$C_4$alkylcarbonyl, $C_1$-$C_6$alkoxycarbonyl, hydroxy, $C_1$-$C_4$alkoxy, $C_3$- or $C_4$-alkenyloxy, $C_3$- or $C_4$-alkynyloxy, $C_1$-$C_4$haloalkoxy, nitro or amino.

Preference is given also to compounds of formula I wherein $R_1$, $R_2$ and $R_3$ are $C_1$-$C_4$alkyl and X is halogen.

Likewise preferred are compounds of formula I wherein n is 0.

Of those, special preference is given to compounds of formula I wherein $R_1$ and $R_3$ are $C_2$-$C_4$alkyl, $R_2$ is $C_1$-$C_3$alkyl, and X is Cl or Br. Especially preferred compounds of formula I are those wherein $R_1$ and $R_3$ are ethyl or propyl, $R_2$ is methyl or ethyl, and X is chloro or bromo. Even more especially preferred compounds of formula I are those wherein n is 0, $R_1$ and $R_3$ are ethyl, $R_2$ is methyl, and X is chloro or bromo.

Preparation of substituted benzenes according to formula I by classical Sandmeyer reactions are known in the art. For example, WO00078712 describes a classical Sandmeyer reaction for the production of 1-bromo-2,6-diethyl-4-methylbenzene.

It has now been found, surprisingly, that a variation of the classical Sandmeyer reaction, wherein gaseous or aqueous acid is employed in non-aqueous Sandmeyer conditions, produces 1-halo-2,6-diethyl-4-methylbenzene in greater yields. More particularly, in a classic Sandmeyer reaction, the diazonium salt is added into a cuprous halide solution, tending to minimize formation of phenol and hydrocarbon coupling reactions. In most cases, the reaction takes place at 0-20° C. and requires the use of a molar amount of cuprous halide to promote the pyrolysis of diazonium salt. In the process of the present invention, metal halide or onium halide is used in the reaction to provide a source of additional solubilized halide ion, further minimizing the phenol formation. Additionally, in case of aqueous acid being employed, water removal by azeotropic distillation helps to minimize the phenol formation, thus improving yields. The diazonium salt is generated in situ, i.e., the diazotization and pyrolysis are carried out simultaneously at elevated temperatures, and the reaction proceeds without the use of copper.

The present process is distinguished by:
a) use of gaseous or aqueous acid in non-aqueous Sandmeyer reactions;
b) use of metal halide or onium halide in the reaction to provide a source of additional solubilized halide ion, further minimizing the phenol formation;
c) in case that aqueous acid is used, water removal by azeotropic distillation helps to minimize phenol formation, thus improving yield of the substituted benzene product;
d) in situ formation of the diazonium salt by simultaneous diazotization and pyrolysis at elevated temperatures;
e) absence of copper reagents necessary for classical Sandmeyer reactions;
f) reduced phenol by-products make it possible to purify the substituted benzene products by vacuum distillation;
g) ability to recover and recycle process chemicals such as solvent and by-product alcohol in the process.

The present preparation process is therefore suitable especially for the cost-effective, large-scale preparation of substituted benzene derivatives of formula I.

The process according to the invention for the preparation of compounds of formula I comprises reacting a compound of formula II

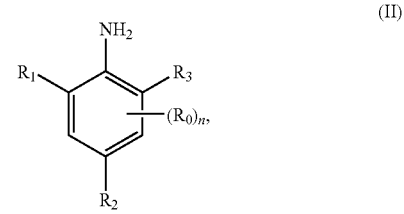

wherein $R_0$, $R_1$, $R_2$, $R_3$ and n are as defined for formula I, with aqueous acid in non-aqueous Sandmeyer reactions in the absence of copper. Water removal by azeotropic distillation minimizes the phenol formation and therefore improves the yield of the compound of formula 1. Alternatively, gaseous acid can be used to replace aqueous acid in the reactions. Consequently, a step of water removal by azeotropic distillation can be eliminated.

The preparation of compounds of formula I is illustrated in the following Reaction Scheme 1.

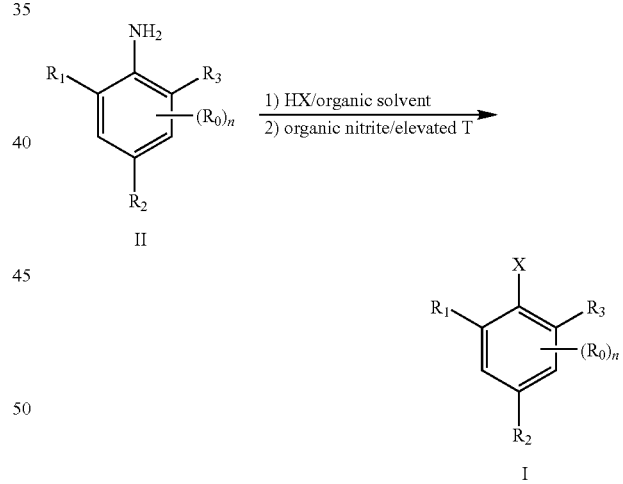

According to Reaction Scheme 1, the compounds of formula I are obtained from the aniline compounds of formula II by reacting the aniline compounds of formula II, in a first reaction step, with aqueous HX acid in a suitable organic solvent to form the aniline.HX salt, followed by water removal via azeotropic distillation. Alternatively, anhydrous aniline.HX salt can be formed directly by the reaction of aniline compound of formula II and gaseous HX acid in a suitable organic solvent. The first step of the process of the present invention may include the addition of a suitable metal halide or onium halides (PTC), to further improve the yield. In the second step of the process of the present invention, addition of an organic nitrite forms the diazonium salt in situ by simultaneously carrying out the diazotization and pyrolysis steps at elevated temperature ranges. Unlike classical Sandmeyer reactions, the process of the present invention proceeds in the absence of copper and produces compounds of formula I in high yield.

Examples of suitable organic solvents for the reaction of compounds of formula II with gaseous or aqueous HX (Step 1 in Reaction Scheme 1) include, for example and not for limitation, dibromomethane, 1,2-dibromoethane, 1,2-dichloroethane, dodecane, heptane, methylcyclohexane, toluene, xylene, chlorobenzene, dichlorobenzene, and mesitylene. o-Dichlorobenzene is a preferred organic solvent.

Examples of suitable metal halides or onium halides useful in Step 1 in Reaction Scheme 1 include, but are not limited to, sodium bromide, potassium bromide, sodium chloride, tetrabutylammonium bromide, tetrabutylphosphonium bromide, and methyltributylammonium chloride.

Examples of suitable organic nitrites useful in Step 2 in Reaction Scheme 1 include, but are not limited to, alkyl nitrites, such as isoamyl nitrite, n-pentyl nitrite, n-butyl nitrite, and t-butyl nitrite.

Reaction conditions proceed at elevated temperatures. In Step 1 of Reaction Scheme 1, the formation of the aniline.HX salt is carried out at reaction temperatures of about 40° to about 55° C., and the reaction thereof with the organic nitrite in the absence of copper or copper reagents (Step 2 in Reaction Scheme 1) is carried out at reaction temperatures of from about 50° to about 55° C. Temperatures during the azeotropic distillation step in Step 1 may reach up to 110° C., preferably about 100° C.

If the starting materials employed are not enantiomerically pure, the compounds of formula I obtained in the above-described process are generally in the form of racemates or diastereoisomeric mixtures which, if desired, can be separated on the basis of their physico-chemical properties according to known methods, such as, for example, fractional crystallisation following salt formation with optically pure bases, acids or metal complexes, or by chromatographic procedures, such as, for example, high-pressure liquid chromatography (HPLC) on acetyl cellulose.

Depending on the substituents $R_0$ to $R_3$, the compounds of formula I may be in the form of geometric and/or optical isomers and isomeric mixtures (atropisomers) or as tautomers and tautomeric mixtures.

The Examples that follow further illustrate the invention without limiting it.

PREPARATION EXAMPLES

Example P1

Preparation of 1-bromo-2,6-diethyl-4-methylbromobenzene with gaseous hydrogen bromide Gaseous hydrogen bromide (1.05 equiv.) is fed into a mixture of 2,6-diethyl-4-methylaniline (1.00 equiv.) and sodium bromide (0.10 equiv.) in o-dichlorobenzene. The resulting salt suspension is cooled to 50° C. Isoamyl nitrite (1.05 equiv.) and additional gaseous hydrogen bromide (0.3 equiv.) are fed subsurface simultaneously at 50-55° C. over a 2-hour period to afford 1-bromo-2,6-diethyl-4-methylbenzene as a yellow to light brown solution. The reaction mass is neutralized with 25% caustic solution (ca. 0.3 equiv.). The bottom aqueous phase is separated off. Isoamyl alcohol and o-dichlorobenzene are sequentially stripped off to produce the crude 2,6-diethyl-4-methylbromobenzene material with an assay of 90% and an isolated yield of 87-90%. The product can be further purified by vacuum distillation at 95° C./5 mmHg to give an assay of 97-99%.

Example P2

Preparation of 1-bromo-2,6-diethyl-4-methybenzene with aqueous hydrobromic acid

48% aqueous hydrobromic acid (1.05 equiv.) is fed into a mixture of diethylmethylaniline (1.00 equiv.) and sodium bromide (0.10 equiv.) in o-dichlorobenzene. Water is then azeotroped off under vacuum. The resulting salt suspension is cooled to 50° C. n-Pentyl nitrite (1.05 equiv.) is fed subsurface at 50-55° C. over 2-hour period to afford 1-bromo-2,6-diethyl-4-methylbenzene as a yellow to light brown solution. The bottom aqueous phase is separated off. The organic phase is washed with 10% sodium carbonate solution (0.15 equiv.). n-Pentanol and o-dichlorobenzene are sequentially stripped off to produce the crude 1-bromo-2,6-diethyl-4-methylbenzene material with an assay of 90% and an isolated yield of 83-85%. The product can be further purified by vacuum distillation at 95° C./5 mmHg to give an assay of 97-99%.

Example P3

Preparation of 1-chloro-2,6-diethyl-4-methylbenzene with gaseous hydrogen chloride Gaseous hydrogen chloride (1.05 equiv.) is fed into a solution of 2,6-diethyl-4-methylaniline (1.00 equiv.) in o-dichlorobenzene, allowing the pot temperature to rise to 70° C. The resulting salt suspension is cooled to 45° C. Isoamyl nitrite (1.05 equiv.) and additional gaseous hydrogen chloride (0.50 equiv.) are fed subsurface simultaneously at 45-50° C. over a 2-hour period to afford 1-chloro-2,6-diethyl-4-methylbenzene in 90-93% yield. 20% sodium hydroxide (0.50 equiv.) is added to adjust the pH to 10-12. The bottom aqueous phase is separated off. Isoamyl alcohol and o-dichlorobenzene are stripped off to produce the crude 1-chloro-2,6-diethyl-4-methylbenzene material. The product can be further purified by vacuum distillation at 85° C./5 mmHg to give an assay of 97-99%.

Example P4

Preparation of 1-chloro-2,6-diethyl-4-methylbenzene with aqueous hydrochloric acid 37% aqueous hydrochloric acid can be used to replace gaseous hydrogen chloride in the process of example P3. An additional step of azeotropic distillation is needed to remove water after 2,6-diethyl-4-methylaniline.HCl salt formation. A drying agent such as $CaCl_2$ or $CaSO_4$ is optionally added in the diazotization step to achieve good yield.

What is claimed is:

1. A process for the preparation of a compound of formula I

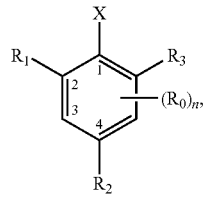

(I)

wherein $R_0$ is, each independently of any other, halogen, $C_1$-$C_6$alkyl, $C_2$-$C_6$alkenyl, $C_2$-$C_6$alkynyl, $C_1$-$C_6$haloalkyl, cyano-$C_1$-$C_6$alkyl, $C_2$-$C_6$haloalkenyl, cyano-$C_2$-$C_6$alkenyl, $C_2$-$C_6$haloalkynyl, cyano-$C_2$-$C_6$alkynyl, hydroxy, hydroxy-$C_1$-$C_6$alkyl, $C_1$-$C_6$alkoxy, nitro, amino, $C_1$-$C_6$alkylamino, di($C_1$-$C_6$alkyl)amino, $C_1$-$C_6$alkylcarbonylamino, $C_1$-$C_6$alkylsulfonylamino, $C_1$-$C_6$alkylaminosulfonyl, $C_1$-$C_6$alkylcarbonyl, $C_1$-$C_6$alkylcarbonyl-$C_1$-$C_6$alkyl, $C_1$-$C_6$-alkoxycarbonyl-$C_1$-$C_6$alkyl, $C_1$-$C_6$alkylcarbonyl-$C_2$-$C_6$alkenyl, $C_1$-$C_6$alkoxycarbonyl, $C_1$-$C_6$alkoxycarbonyl-$C_2$-$C_6$alkenyl, $C_1$-$C_6$alkylcarbonyl-$C_2$-$C_6$alkynyl, $C_1$-$C_6$alkoxycarbonyl-$C_2$-$C_6$alkynyl, cyano, carboxyl, phenyl or an aromatic ring that contains 1 or 2 hetero atoms selected from the group consisting of nitrogen, oxygen and sulfur, wherein the latter two aromatic rings may be substituted by $C_1$-$C_3$alkyl, $C_1$-$C_3$haloalkyl, $C_1$-$C_3$alkoxy, $C_1$-$C_3$haloalkoxy, halogen, cyano or by nitro; or $R_0$, together with the adjacent substituents $R_1$, $R_2$ and $R_3$, forms a saturated or unsaturated $C_3$-$C_6$hydrocarbon bridge that may be interrupted by 1 or 2 hetero atoms selected from the group consisting of nitrogen, oxygen and sulfur and/or substituted by $C_1$-$C_4$alkyl;

$R_1$, $R_2$ and $R_3$ are, each independently of the others, hydrogen, halogen, $C_1$-$C_6$alkyl, $C_2$-$C_6$-alkenyl, $C_2$-$C_6$alkynyl, $C_3$-$C_6$cycloalkyl, $C_1$-$C_6$haloalkyl, $C_2$-$C_6$haloalkenyl, $C_1$-$C_6$alkoxy-carbonyl-$C_2$-$C_6$alkenyl, $C_1$-$C_6$alkylcarbonyl-$C_2$-$C_6$alkenyl, cyano-$C_2$-$C_6$alkenyl, nitro-$C_2$-$C_6$-alkenyl, $C_2$-$C_6$haloalkynyl, $C_1$-$C_6$alkoxycarbonyl-$C_2$-$C_6$alkynyl, $C_1$-$C_6$alkylcarbonyl-$C_2$-$C_6$-alkynyl, cyano-$C_2$-$C_6$alkynyl, nitro-$C_2$-$C_6$alkynyl, $C_3$-$C_6$halocycloalkyl, hydroxy-$C_1$-$C_6$alkyl, $C_1$-$C_6$alkoxy-$C_1$-$C_6$alkyl, $C_1$-$C_6$alkylthio-$C_1$-$C_6$alkyl, cyano, $C_1$-$C_4$alkylcarbonyl, $C_1$-$C_6$-alkoxycarbonyl, hydroxy, $C_1$-$C_{10}$alkoxy, $C_3$-$C_6$alkenyloxy, $C_3$-$C_6$alkynyloxy, $C_1$-$C_6$haloalkoxy, $C_3$-$C_6$haloalkenyloxy, $C_1$-$C_6$alkoxy-$C_1$-$C_6$alkoxy, mercapto, $C_1$-$C_6$alkylthio, $C_1$-$C_6$haloalkylthio, $C_1$-$C_6$alkylsulfinyl, $C_1$-$C_6$alkylsulfonyl, nitro, amino, $C_1$-$C_6$alkylamino, di($C_1$-$C_6$alkyl)amino or phenoxy in which the phenyl ring may be substituted by $C_1$-$C_3$alkyl, $C_1$-$C_3$haloalkyl, $C_1$-$C_3$-alkoxy, $C_1$-$C_3$haloalkoxy, halogen, cyano or by nitro;

$R_2$ also may be phenyl, naphthyl or a 5- or 6-membered aromatic ring that may contain 1 or 2 hetero atoms selected from the group consisting of nitrogen, oxygen and sulfur, wherein the phenyl ring, the naphthyl ring system and the 5- or 6-membered aromatic ring may be substituted by halogen, $C_3$-$C_8$cycloalkyl, hydroxy, mercapto, amino, cyano, nitro or by formyl; and/or the phenyl ring, the naphthyl ring system and the 5- or 6-membered aromatic ring may be substituted by $C_1$-$C_6$alkyl, $C_1$-$C_6$alkoxy, hydroxy-$C_1$-$C_6$alkyl, $C_1$-$C_6$alkoxy-$C_1$-$C_6$alkyl, $C_1$-$C_6$-alkoxy-$C_1$-$C_6$alkoxy, $C_1$-$C_6$alkylcarbonyl, $C_1$-$C_6$alkylthio, $C_1$-$C_6$alkylsulfinyl, $C_1$-$C_6$alkylsulfonyl, mono-$C_1$-$C_6$alkylamino, di($C_1$-$C_6$alkyl)amino, $C_1$-$C_6$alkylcarbonylamino, $C_1$-$C_6$alkylcarbonyl($C_1$-$C_6$alkyl)amino, $C_2$-$C_6$alkenyl, $C_3$-$C_6$alkenyloxy, hydroxy-$C_3$-$C_6$alkenyl, $C_1$-$C_6$alkoxy-$C_2$-$C_6$alkenyl, $C_1$-$C_6$alkoxy-$C_3$-$C_6$alkenyloxy, $C_2$-$C_6$alkenylcarbonyl, $C_2$-$C_6$alkenylthio, $C_2$-$C_6$alkenylsulfinyl, $C_2$-$C_6$alkenylsulfonyl, mono- or di-($C_2$-$C_6$alkenyl)amino, $C_1$-$C_6$alkyl($C_3$-$C_6$alkenyl)amino, $C_2$-$C_6$alkenylcarbonylamino, $C_2$-$C_6$alkenylcarbonyl($C_1$-$C_6$alkyl)amino, $C_2$-$C_6$alkynyl, $C_3$-$C_6$alkynyloxy, hydroxy-$C_3$-$C_6$alkynyl, $C_1$-$C_6$alkoxy-$C_3$-$C_6$alkynyl, $C_1$-$C_6$alkoxy-$C_4$-$C_6$alkynyloxy, $C_2$-$C_6$alkynylcarbonyl, $C_2$-$C_6$alkynylthio, $C_2$-$C_6$alkynylsulfinyl, $C_2$-$C_6$alkynylsulfonyl, mono- or di-($C_3$-$C_6$alkynyl)amino, $C_1$-$C_6$alkyl($C_3$-$C_6$alkynyl)amino, $C_2$-$C_6$alkynylcarbonylamino or by $C_2$-$C_6$alkynylcarbonyl($C_1$-$C_6$alkyl)amino; and/or the phenyl ring, the naphthyl ring system and the 5- or 6-membered aromatic ring may be substituted by halo-substituted $C_1$-$C_6$alkyl, $C_1$-$C_6$alkoxy, hydroxy-$C_1$-$C_6$alkyl, $C_1$-$C_6$alkoxy-$C_1$-$C_6$alkyl, $C_1$-$C_6$alkoxy-$C_1$-$C_6$alkoxy, $C_1$-$C_6$alkylcarbonyl, $C_1$-$C_6$alkylthio, $C_1$-$C_6$alkylsulfinyl, $C_1$-$C_6$alkylsulfonyl, mono-$C_1$-$C_6$alkylamino, di($C_1$-$C_6$alkyl)amino, $C_1$-$C_6$alkylcarbonylamino, $C_1$-$C_6$alkylcarbonyl($C_1$-$C_6$alkyl)amino, $C_2$-$C_6$alkenyl, $C_3$-$C_6$alkenyloxy, hydroxy-$C_3$-$C_6$alkenyl, $C_1$-$C_6$alkoxy-$C_2$-$C_6$alkenyl, $C_1$-$C_6$alkoxy-$C_3$-$C_6$alkenyloxy, $C_2$-$C_6$alkenylcarbonyl, $C_2$-$C_6$-alkenylthio, $C_2$-$C_6$alkenylsulfinyl, $C_2$-$C_6$alkenylsulfonyl, mono- or di-($C_2$-$C_6$alkenyl)amino, $C_1$-$C_6$-alkyl($C_3$-$C_6$alkenyl)amino, $C_2$-$C_6$alkenylcarbonylamino, $C_2$-$C_6$alkenylcarbonyl($C_1$-$C_6$-alkyl)amino, $C_2$-$C_6$alkynyl, $C_3$-$C_6$alkynyloxy, hydroxy-$C_3$-$C_6$alkynyl, $C_1$-$C_6$alkoxy-$C_3$-$C_6$alkynyl, $C_1$-$C_6$alkoxy-$C_4$-$C_6$alkynyloxy, $C_2$-$C_6$alkynylcarbonyl, $C_2$-$C_6$alkynylthio, $C_2$-$C_6$alkynylsulfinyl, $C_2$-$C_6$alkynylsulfonyl, mono- or di-($C_3$-$C_6$alkynyl)amino, $C_1$-$C_6$alkyl($C_3$-$C_6$alkynyl)amino, $C_2$-$C_6$alkynylcarbonylamino or $C_2$-$C_6$alkynylcarbonyl($C_1$-$C_6$alkyl)amino; and/or the phenyl ring, the naphthyl ring system and the 5- or 6-membered aromatic ring may be substituted by a radical of formula $COOR_{50}$, $CONR_{51}$, $SO_2NR_{53}R_{54}$ or $SO_2OR_{55}$, wherein $R_{50}$, $R_{51}$, $R_{52}$, $R_{53}$, $R_{54}$ and $R_{55}$ are, each independently of the others, $C_1$-$C_6$alkyl, $C_2$-$C_6$alkenyl or $C_3$-$C_6$alkynyl or halo-, hydroxy-, alkoxy-, mercapto-, amino-, cyano-, nitro-, alkylthio-, alkylsulfinyl- or alkylsulfonyl-substituted $C_1$-$C_6$alkyl, $C_2$-$C_6$alkenyl or $C_3$-$C_6$alkynyl;

X is chloro or bromo; and n is 0, 1 or 2;

which comprises (a) reacting a compound of formula (II)

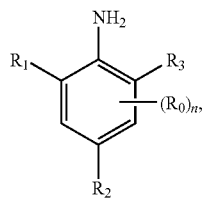

with gaseous or aqueous HX in an organic solvent, wherein X is as defined above for formula (I);

(b) removing water by azeotropic distillation in case that aqueous HX is used; and (c) adding an organic nitrite in the absence of copper.

2. The process according to claim 1, wherein $R_1$, $R_2$ and $R_3$ are independently $C_1$-$C_6$ alkyl and n is 0.

3. The process according to claim 2, wherein $R_1$ and $R_3$ are ethyl, and $R_2$ is methyl.

4. The process according to claim 3, wherein the organic solvent is selected from the group consisting of dibromomethane, 1,2-dibromoethane, 1,2-dichloroethane, dodecane, heptane, methylcyclohexane, toluene, o-xylene, chlorobenzene, o-dichlorobenzene, and mesitylene.

5. The process according to claim 3, wherein the organic nitrite is selected from the group consisting of isoamyl nitrite, n-pentyl nitrite, n-butyl nitrite, and t-butyl nitrite.

6. The process according to claim 3, wherein step (a) further comprises adding a metal halide or onium halide, wherein halide is X and is as defined for formula (I).

7. The process according to claim 3, wherein the azeotropic distillation of step (b) takes place at a temperature between about 50-110° C.

8. The process according to claim 3, wherein the temperature of step (c) is between 40-100° C.

9. The process according to claim 3, further comprising removing water by-product and residual acid by neutralization with an inorganic base and phase separation.

10. The process according to claim 9, further comprising distilling off and recycling of by-product alcohol and organic solvent.

11. The process according to claim 10, further comprising purifying the compound of formula (I) formed by the process by vacuum distillation.

12. The process according to claim 1 to produce a compound of formula (I) wherein X is bromo, which comprises (a) reacting a compound of formula II

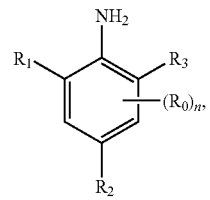

wherein n is 0, $R_1$ and $R_3$ are ethyl, and $R_2$ is methyl, with gaseous or aqueous HBr in o-dichlorobenzene;

(b) removing water by azeotropic distillation at a vacuum pressure until the temperature reaches about 100° C. in the case that aqueous HBr is employed; and (c) adding n-pentyl nitrite at a temperature of about 45-55° C.;

(d) removing water by-product and residual acid by neutralization with an organic base selected from sodium hydroxide and sodium carbonate, followed by phase separation;

(e) purifying the compound of formula (I) by vacuum distillation.

13. The process according to claim 12, wherein sodium bromide is added to the reaction in (a).

14. The process according to claim 1, to produce a compound of formula (I) wherein X is chloro, which comprises (a) reacting a compound of formula II

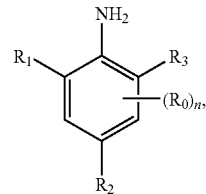

wherein n is 0, $R_1$ and $R_3$ are ethyl, and $R_2$ is methyl, with gaseous or aqueous HCl in o-dichlorobenzene;

(b) removing water by azeotropic distillation at a vacuum pressure until the temperature reaches about 100° C. in case that aqueous HCl is employed; and (c) adding isoamyl nitrite at a temperature of about 44-50° C.;

(d) removing water by-product and residual acid by neutralization with an organic base selected from sodium hydroxide and sodium carbonate, followed by phase separation;

(f) purifying the compound of formula (I) by vacuum distillation.

15. The process according to claim 14, wherein sodium chloride is added to the reaction in (a).

* * * * *